US009913783B2

(12) United States Patent
Strand et al.

(10) Patent No.: US 9,913,783 B2
(45) Date of Patent: Mar. 13, 2018

(54) DENTIFRICE COMPOSITIONS HAVING OPTIMIZED PRESERVATIVES

(71) Applicant: The Procter & Gamble Company, Cincinnati, OH (US)

(72) Inventors: Ross Strand, Beijing (CN); Wei Wei, Beijing (CN); Hongmei Yang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/682,141

(22) Filed: Apr. 9, 2015

(65) Prior Publication Data
US 2015/0328105 A1 Nov. 19, 2015

(51) Int. Cl.
A61Q 11/00 (2006.01)
A61K 8/19 (2006.01)
A61K 8/34 (2006.01)
A61K 8/37 (2006.01)
A61K 8/73 (2006.01)
A61K 8/21 (2006.01)
A61K 8/25 (2006.01)

(52) U.S. Cl.
CPC .................. A61K 8/19 (2013.01); A61K 8/25 (2013.01); A61K 8/34 (2013.01); A61K 8/37 (2013.01); A61K 8/73 (2013.01); A61K 8/731 (2013.01); A61Q 11/00 (2013.01); A61K 2800/28 (2013.01); A61K 2800/48 (2013.01); A61K 2800/524 (2013.01)

(58) Field of Classification Search
USPC .............................................. 424/49, 52, 55
See application file for complete search history.

(56) References Cited

U.S. PATENT DOCUMENTS

| | | | |
|---|---|---|---|
| 3,119,743 A | 1/1964 | Ericsson | |
| 4,046,872 A | 9/1977 | Mitchell et al. | |
| 4,283,385 A | 8/1981 | Dhabhar et al. | |
| 4,404,599 A | 9/1983 | Kinjo et al. | |
| 4,565,691 A | 1/1986 | Jackson | |
| 4,678,662 A | 7/1987 | Chan | |
| 4,701,319 A | 10/1987 | Woo | |
| 4,828,849 A | 5/1989 | Lynch et al. | |
| 5,939,052 A | 8/1999 | White, Jr. et al. | |
| 6,106,811 A | 8/2000 | Gibbs | |
| 6,159,446 A | 12/2000 | Randive et al. | |
| 6,696,045 B2 | 2/2004 | Yue et al. | |
| 6,759,876 B2 | 7/2004 | Inoue et al. | |
| 6,855,325 B1 | 2/2005 | Yvin et al. | |
| 7,648,363 B2 | 1/2010 | Oniki et al. | |
| 8,007,771 B2 | 8/2011 | Ramji et al. | |
| 2002/0001569 A1 | 1/2002 | Dromard | |
| 2003/0072721 A1 | 4/2003 | Riley et al. | |
| 2003/0095931 A1 | 5/2003 | Stier | |
| 2003/0103914 A1* | 6/2003 | Lawlor | A23G 3/36 424/58 |
| 2004/0120902 A1 | 6/2004 | Wernett et al. | |
| 2004/0131560 A1 | 7/2004 | Corcoran et al. | |
| 2006/0134020 A1 | 6/2006 | Robinson et al. | |
| 2006/0159631 A1 | 7/2006 | Buch et al. | |
| 2007/0231278 A1 | 10/2007 | Lee et al. | |
| 2008/0230298 A1 | 9/2008 | Buch et al. | |
| 2009/0136584 A1 | 5/2009 | Hosoya et al. | |
| 2009/0269287 A1 | 10/2009 | Berta | |
| 2010/0086498 A1 | 4/2010 | Haught et al. | |
| 2012/0189561 A1 | 7/2012 | Randive et al. | |
| 2013/0064779 A1 | 3/2013 | Yamane et al. | |
| 2013/0280182 A1 | 10/2013 | Burgess et al. | |
| 2013/0280183 A1* | 10/2013 | Salazar Navarrete | A61K 8/37 424/52 |
| 2013/0344120 A1 | 12/2013 | Scott et al. | |
| 2014/0314690 A1 | 10/2014 | Fisher et al. | |

FOREIGN PATENT DOCUMENTS

| | | |
|---|---|---|
| CN | 101690699 A | 4/2010 |
| CN | 102283794 A | 12/2011 |
| CN | 102283795 A | 12/2011 |
| EP | 2057978 A1 | 5/2009 |
| KR | 2002/0054045 A | 7/2002 |
| KR | 2012/0042399 A | 5/2012 |
| WO | WO 2007/122146 | 11/1987 |
| WO | WO1998022079 A1 | 5/1998 |
| WO | WO2003/017964 A1 | 8/2002 |
| WO | WO2005058364 A2 | 6/2005 |
| WO | WO2007076001 A2 | 7/2007 |
| WO | WO2008005548 A2 | 1/2008 |
| WO | WO2008041055 A1 | 4/2008 |
| WO | WO2010114546 A1 | 10/2010 |
| WO | WO2011031807 A2 | 3/2011 |
| WO | WO2011157497 A1 | 12/2011 |
| WO | WO2013034421 A2 | 3/2013 |
| WO | WO2013094312 A1 | 6/2013 |
| WO | WO2015094152 A1 | 6/2015 |
| WO | WO2015094154 A1 | 6/2015 |

OTHER PUBLICATIONS

Uzel et al. Microbiological Research, 160, 2005, pp. 189-195.*
Pearce, et al. "The Effect of pH, Temperature and Plaque Thickness on the Hydrolysis of Monofluorophosphate in Experimental Dental Plaque", Caries Research, vol. 37, pp. 178-184, Feb. 1, 2003.
PCT International Search Report for PCT/CN2014/077527 dated Feb. 10, 2015.
PCT/CN2014/077427 International Search Report and Written Opinion dated Feb. 17, 2016.

(Continued)

Primary Examiner — Lezah Roberts
(74) Attorney, Agent, or Firm — Parker D. McCrary; Alexandra S. Anoff

(57) ABSTRACT

A dentifrice composition comprising 45% to 75% water, by weight of the composition; 25% to 50% of a calcium-containing abrasive by weight of the composition; greater than 0.10% to 0.30% benzyl alcohol, by weight of the composition; 0.01% to 0.11% of a paraben by weight of the composition; and an alkaline pH.

20 Claims, 1 Drawing Sheet

(56) References Cited

OTHER PUBLICATIONS

PCT/CN2014/077536 International Search Report and Written Opinion dated May 15, 2014.
PCT/CN2015/077634 International Search Report and Written Opinion dated Jul. 22, 2015.
PCT/CN2015/077634 Supplementary International Search Report and Written Opinion lated Feb. 26, 2016.
PCT/CN2015/077636 International Search Report and Written Opinion.
EP 15793035 Supplementary European Search Report dated Oct. 20, 2017.
All Office Actions, U.S. Pat. No. 9,687,427.
All Office Actions, U.S. Appl. No. 14/633,389.
All Office Actions, U.S. Pat. No. 9,498,416.
All Office Actions, U.S. Appl. No. 15/294,855.
All Office Actions, U.S. Appl. No. 14/634,969.
All Office Actions, U.S. Appl. No. 14/635,234.
All Office Actions, U.S. Appl. No. 14/700,182.
All Office Actions, U.S. Appl. No. 14/830,815.
All Office Actions, U.S. Appl. No. 14/634,993.
All Office Actions, U.S. Appl. No. 14/830,831.
All Office Actions, U.S. Appl. No. 14/634,949.
All Office Actions, U.S. Pat. No. 9,364,419.
All Office Actions, U.S. Appl. No. 15/150,486.
All Office Actions, U.S. Appl. No. 14/682,146.
All Office Actions, U.S. Appl. No. 14/700,196.
All Office Actions, U.S. Appl. No. 14/830,839.
All Office Actions, U.S. Appl. No. 14/736,352.
PCT/CN2014/077527 Supplementary International Search Report and Written Opinion dated Jul. 27, 2016.

\* cited by examiner

| Components: (wt%) | Ex 1 | Ex 2 | Ex 3 | Ex 4 | Ex 5 | Ex 6 | Ex 7 | Ex 8 Control B | Ex 9 Control C | Ex 10 Control D | Ex 11 Control A |
|---|---|---|---|---|---|---|---|---|---|---|---|
| Water | 59.89 | 60.07 | 59.9 | 59.94 | 60 | 60.04 | 59.78 | 60.18 | 60.1 | 59.98 | 60.67 |
| Sodium Carboxymethyl Cellulose | 0.91 | 0.91 | 0.91 | 0.91 | 0.91 | 0.91 | 0.91 | 0.91 | 0.91 | 0.91 | 0.91 |
| Carrageenan | 1.20 | 1.2 | 1.2 | 1.2 | 1.2 | 1.2 | 1.2 | 1.2 | 1.2 | 1.2 | 1.2 |
| Thickening Silica | 2.62 | 2.62 | 2.62 | 2.62 | 2.62 | 2.62 | 2.62 | 2.62 | 2.62 | 2.62 | 2.62 |
| Calcium Carbonate | 32. | 32 | 32 | 32 | 32 | 32 | 32 | 32 | 32 | 32 | 32 |
| Sodium Lauryl Sulfate | 2.1 | 2.1 | 2.1 | 2.1 | 2.1 | 2.1 | 2.1 | 2.1 | 2.1 | 2.1 | 2.1 |
| Sodium Carbonate | 0.5 | 0.5 | 0.5 | 0.5 | 0.5 | 0.5 | 0.5 | 0.5 | 0.5 | 0.5 | 0.5 |
| Menthol | 0.49 | 0.49 | 0.49 | 0.49 | 0.49 | 0.49 | 0.49 | 0.49 | 0.49 | 0.49 | 0 |
| Benzyl Alcohol | 0.29 | 0 | 0.2 | 0.2 | 0.1 | 0.1 | 0.29 | 0 | 0 | 0.2 | 0 |
| Methyl paraben | 0 | 0.07 | 0.05 | 0.03 | 0.05 | 0.03 | 0.07 | 0 | 0.05 | 0 | 0 |
| Propyl paraben | 0 | 0.04 | 0.03 | 0.01 | 0.03 | 0.01 | 0.04 | 0 | 0.03 | 0 | 0 |
| Total | 100.00 | 100.00 | 100.00 | 100.00 | 100.00 | 100.00 | 100.00 | 100.00 | 100.00 | 100.00 | 100.00 |
| pH | 9.63 | 9.38 | 9.46 | 9.49 | 9.52 | 9.68 | 9.59 | 9.69 | 9.57 | 9.56 | 9.9 |

US 9,913,783 B2

DENTIFRICE COMPOSITIONS HAVING OPTIMIZED PRESERVATIVES

CROSS REFERENCE TO RELATED APPLICATION

This application claims the benefit of Application No. CN2014/077527, filed May 15, 2014.

FIELD OF THE INVENTION

The present invention relates to dentifrice compositions having optimized preservatives and preservative levels.

BACKGROUND OF THE INVENTION

Dentifrice compositions are well known for dental and oral hygiene care. High water (e.g., >45 wt %) and high carbonate (e.g., >25 wt %) formulation chassis are cost effective for many markets and consumers. These compositions are typically formulated at a higher pH given the carbonate content. Benzyl alcohol and parabens are generally known as preservatives. However, there is a need to reduce their use for cost and other reasons. It is also well known that each microbe species has a preferred pH range and a pH tolerance range. *Halomonas* is a well known genus of bacteria that is known to be able to grow in alkaline pH. Many approaches for optimizing preservatives in dentifrice formulations are directed to neutral pH systems (as in silicate based dentifrice formulations). However, there is a need to optimize preservatives in a high pH (e.g., pH~9) system and to do so based-upon a microbe system that is more relevant to this high pH system.

SUMMARY OF THE INVENTION

The present invention is based, in part, on the surprising observations that there is synergy in certain levels of benzyl alcohol and paraben in high water and high carbonate dentifrice formulations in achieving maximum log reduction of a *Halomonas* strain. It is surprisingly observed that typical levels of benzyl alcohol and paraben can achieve maximum log reduction of *Halomonas* within 24 hours. Yet further surprising observations indicate that certain lower levels of benzyl alcohol and paraben can still achieve maximum log reduction of *Halomonas* within 72 hours.

One advantage is the high water and high carbonate dentifrice formulation achieves maximum *Halomonas* kill reduction within 24 hours by the synergistic combination of benzyl alcohol and paraben.

Another advantage is the high water and high carbonate dentifrice formulation achieves maximum *Halomonas* kill reduction within 72 hours by the synergistic combination of benzyl alcohol and paraben while minimizing the use of these ingredients.

One aspect of the invention provides a dentifrice composition comprising: (a) 45% to 75% water, preferably 50% to 60% water, by weight of the composition; (b) 25% to 50%, preferably 27% to 47%, preferably 27% to 37% of a calcium-containing abrasive by weight of the composition, preferably wherein the calcium-containing abrasive comprises calcium carbonate; (c) greater than 0.10% to 0.30%, preferably 0.15% to 0.25%, more preferably 0.17% to 0.23% of benzyl alcohol by weight of the composition; (d) 0.01% to 0.11%, preferably 0.02% to 0.10%, more preferably 0.03% to 0.09% of a paraben by weight of the composition; and (e) an alkaline pH. In one embodiment, the alkaline pH is greater than 8.0, preferably greater than 8.5, more preferably at or greater than pH 9, alternatively a pH from 8 to 13, alternatively from 9 to 12, alternatively combinations thereof. In another embodiment, the paraben is selected from methyl paraben, propyl paraben, or combinations thereof; alternatively wherein there is a greater weight ratio of methyl paraben to propyl paraben. In yet still another embodiment, the dentifrice composition further comprises from 0.0025% to 2%, preferably from 0.5% to 1.5% of a fluoride ion source by weight of the composition, preferably wherein the fluoride ion source is sodium monofluorophosphate.

In one embodiment, the dentifrice composition further comprises from 0.1% to 12% of a surfactant by weight of the composition, preferably 1% to 9% of the surfactant, more preferably wherein the surfactant is an anionic surfactant, yet more preferably wherein the anionic surfactant is sodium lauryl sulfate. In yet another embodiment, the composition further comprises 0.01 to 2% of menthol.

In one embodiment, the composition further comprises a binder. For example, the binder may comprise: (a) 0.01% to less than 1.4%, preferably from 0.1% to 1.3%, more preferably from 0.5% to 1.3% of a carrageenan by weight of the composition; and (b) greater than 0.4% to 2%, preferably from 0.5% to 1.8%, more preferably from 0.6% to 1.8% of a carboxymethyl cellulose by weight of the composition. In a further embodiment, the binder further comprises 0.5% to 5%, preferably 1% to 4%, of a thickening silica by weight of the composition.

Yet another aspect of the invention provides a method of treating tooth enamel comprising the step of brushing teeth with a dentifrice composition herein described.

While the specification concludes with claims that particularly point out and distinctly claim the invention, it is believed the present invention will be better understood from the following description.

BRIEF DESCRIPTION OF THE DRAWINGS

FIG. 1 describes dentifrice formulations of Examples 1-11, wherein Examples 8, 9, 10, and 11 are control formulations.

DETAILED DESCRIPTION OF THE INVENTION

Definitions

The term "orally acceptable carrier" as used herein means a suitable vehicle or ingredient, which can be used to form and/or apply the present compositions to the oral cavity in a safe and effective manner.

The term "comprising" as used herein means that steps and ingredients other than those specifically mentioned can be added. This term encompasses the terms "consisting of" and "consisting essentially of" The compositions of the present invention can comprise, consist of, and consist essentially of the essential elements and limitations of the invention described herein, as well as any of the additional or optional ingredients, components, steps, or limitations described herein.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one embodiment, "effective amount"

means at least 0.01% of the material, by weight of the composition, alternatively at least 0.1%.

The term "dentifrice" as used herein means paste, gel, powder, tablets, or liquid formulations, unless otherwise specified, that are used to clean the surfaces of the oral cavity. The term "teeth" as used herein refers to natural teeth as well as artificial teeth or dental prosthesis.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Preservatives

The dentifrice compositions of the present invention comprise benzyl alcohol and paraben. The paraben may comprise methyl paraben or propyl paraben or combination thereof. Levels of benzyl alcohol may comprise from greater than 0.10% to 0.30%, preferably 0.15% to 0.25%, more preferably 0.17% to 0.23%, alternatively from 0.18% to 0.22%, alternatively from 0.19% to 0.21%, alternatively about 0.2%, alternatively combinations thereof, of benzyl alcohol by weight of the composition. Levels of paraben may comprise from 0.01% to 0.11%, preferably 0.02% to 0.10%, more preferably 0.03% to 0.09%, alternatively combinations thereof, of a paraben by weight of the composition. In one embodiment, the composition comprises from 0.005% to 0.01%, preferably from 0.01% to 0.05%, alternatively from 0.01% to 0.03%, alternatively combinations thereof, of propyl paraben by weight of the composition. In another embodiment, the composition comprises from 0.01% to 0.1%, preferably from 0.02% to 0.07%, alternatively from 0.03% to 0.05%, alternatively combinations thereof of methyl paraben by weight of the composition.

In yet another embodiment, the paraben comprises a combination of methyl paraben and propyl paraben, wherein there is a greater weight ratio of methyl paraben to propyl paraben. In yet still another embodiment, the paraben is methyl paraben and propyl paraben, wherein the weight ratio of methyl paraben to propyl paraben is from 5:3 to 15:3, preferably greater than 5:3 to 15:3, more preferably from 6:3 to 15:3, yet more preferably from 7:3 to 12:3, alternatively from 7:3 to 11:3, alternatively combinations thereof, respectively.

In one embodiment, the dentifrice compositions of the present invention are substantially free of triclosan (i.e., 5-chloro-2-(2,4-dichlorophenoxy)phenol), preferably free of triclosan.

One aspect of the present invention comprises a composition that achieves maximum reduction of a *Halomonas* strain within 72 hours, alternatively within 48 hours, alternatively within 24 hours, alternatively within 3 hours, of being inoculated with the strain, according to the USP/NF or European Pharmacopoeia method described below.

Water

The compositions of the present invention comprise herein from 45% to 75%, by weight of the composition of water. In one embodiment, the composition includes from 40% to 70%, alternatively from 45% to 65%, alternatively from 40% to 60%, alternatively from 50% to 70%, alternatively from 50% to 60%, alternatively from 45% to 55%, alternatively from 55% to 65%, alternatively from 50% to 60%, alternatively about 55%, alternatively combinations thereof, of water by weight of the composition. The water may be added to the formulation and/or may come into the composition from the inclusion of other ingredients. Preferably the water is USP water.

Calcium-Containing Abrasive

The compositions of the present invention comprise from 25% to 50% by weight of a calcium-containing abrasive, wherein the calcium-containing abrasive is selected from the group consisting of calcium carbonate, dicalcium phosphate, tricalcium phosphate, calcium orthophosphate, calcium metaphosphate, calcium polyphosphate, calcium oxyapatite, sodium carbonate, and combinations thereof. In preferred embodiment, the composition comprises from 25% to 60%, more preferably from 25% to 50%, even more preferably from 25% to 40%, yet even more preferably from 26% to 39%, alternatively from 27% to 47%, alternatively from 27% to 37%, alternatively from 30% to 35%, alternatively from 30% to 34%, alternatively combinations thereof, of a calcium-containing abrasive by weight of the composition.

In one embodiment, the calcium-containing abrasive is calcium carbonate. In a preferred embodiment, the calcium-containing abrasive is selected from the group consisting of fine ground natural chalk, ground calcium carbonate, precipitated calcium carbonate, and combinations thereof.

Fine ground natural chalk (FGNC) is one of the more preferred calcium-containing abrasives useful in the present invention. It is obtained from limestone or marble. FGNC may also be modified chemically or physically by coating during milling or after milling by heat treatment. Typical coating materials include magnesium stearate or oleate. The morphology of FGNC may also be modified during the milling process by using different milling techniques, for example, ball milling, air-classifier milling or spiral jet milling. One example of natural chalk is described in WO 03/030850 having a medium particle size of 1 to 15 μm and a BET surface area of 0.5 to 3 $m^2/g$. The natural calcium carbonate may have a particle size of 325 to 800 mesh, alternatively a mess selected from 325, 400 600, 800, or combinations thereof; alternatively the particle size is from 0.1 to 30 microns, or from 0.1 to 20 microns, or from 5 to 20 microns In one embodiment, the composition of the present invention is free or substantially free of silicate.

PEG

The compositions of the present invention may comprise polyethylene glycol (PEG), of various weight percentages of the composition as well as various ranges of average molecular weights. In one aspect of the invention, the compositions have from 0.1% to 15%, preferably from 0.2% to 12%, more preferably from 0.3% to 10%, yet more preferably from 0.5% to 7%, alternatively from 1% to 5%, alternatively from 1% to 4%, alternatively from 1% to 2%, alternatively from 2% to 3%, alternatively from 4% to 5%, or combinations thereof, of PEG by weight of the composition. In another aspect of the invention, the PEG is one having a range of average molecular weight from 100 Daltons to 1600 Daltons, preferably from 200 to 1000, alternatively from 400 to 800, alternatively from 500 to 700 Daltons, alternatively combinations thereof. PEG is a water soluble linear polymer formed by the addition reaction of ethylene oxide to an ethylene glycol equivalent having the general formula is: H—(OCH$_2$CH$_2$)$_n$—OH. One supplier of PEG is Dow Chemical Company under the brandname of CARBOWAX™.

Sweetener

The oral care compositions herein may include a sweetening agent. These include sweeteners such as saccharin, dextrose, sucrose, lactose, maltose, levulose, aspartame, sodium cyclamate, D-tryptophan, dihydrochalcones, acesulfame, sucralose, neotame, and mixtures thereof. Sweetening agents are generally used in oral compositions at levels of from 0.005% to 5%, by weight of the composition, alternatively 0.01% to 1%, alternatively from 0.1% to 0.5%, alternatively combinations thereof.

Fluoride Ion Source

The compositions may include an effective amount of an anti-caries agent. In one embodiment, the anti-caries agent is a fluoride ion source. The fluoride ion may be present in an amount sufficient to give a fluoride ion concentration in the composition at 25° C., and/or in one embodiment can be used at levels of from about 0.0025% to about 5% by weight of the composition, alternatively from about 0.005% to about 2.0% by weight of the composition, to provide anti-caries effectiveness. Examples of suitable fluoride ion-yielding materials are disclosed in U.S. Pat. Nos. 3,535,421, and 3,678,154. Representative fluoride ion sources include: stannous fluoride, sodium fluoride, potassium fluoride, amine fluoride, sodium monofluorophosphate, and zinc fluoride. In one embodiment the dentifrice composition contains a fluoride source selected from stannous fluoride, sodium fluoride, and mixtures thereof. In one embodiment, the fluoride ion source is sodium monofluorophosphate, and wherein the composition comprises 0.0025% to 2% of the sodium monofluorophosphate by weight of the composition, alternatively from 0.5% to 1.5%, alternatively from 0.6% to 1.7%, alternatively combinations thereof. In another embodiment, the composition comprises from 0.0025% to 2% of a fluoride ion source by weight of the composition.

pH

The pH of the dentifrice composition may be greater than pH 7.8, or from pH 8 to 13, more preferably from 9 to 12, alternatively greater than pH 8, alternatively greater than 9, alternatively from 9 to 11, alternatively from 9 to 10, or combinations thereof.

A method for assessing pH of dentifrice is described. pH is measured by a pH Meter with Automatic Temperature Compensating (ATC) probe. The pH Meter is capable of reading to 0.001 pH unit. The pH electrode may be selected from one of the following (i) Orion Ross Sure-Flow combination: Glass body—VWR #34104-834/Orion #8172BN or VWR#10010-772/Orion #8172BNWP; Epoxy body—VWR #34104-830/Orion #8165BN or VWR#10010-770/Orion #8165BNWP; Semi-micro, epoxy body—VWR #34104-837/Orion #8175BN or VWR#10010-774/Orion #3175BNWP; or (ii) Orion PerpHect combination: VWR #34104-843/Orion #8203BN semi-micro, glass body; or (iii) suitable equivalent. The automatic temperature compensating probe is Fisher Scientific, Cat #13-620-16.

A 25% by weight slurry of dentifrice is prepared with deionized water, and thereafter is centrifuged for 10 minutes at 15000 rotations-per-minute using a SORVALL RC 28S centrifuge and SS-34 rotor (or equivalent gravitational force, at 24149 g force). The pH is assessed in supernatant after one minute or the taking reading is stabilized. After each pH assessment, the electrode is washed with deionized water. Any excess water is wiped with a laboratory grade tissue. When not in issue, the electrode is kept immersed in a pH 7 buffer solution or an appropriate electrode storage solution.

pH Modifying Agent

The dentifrice compositions herein may include an effective amount of a pH modifying agent, alternatively wherein the pH modifying agent is a pH buffering agent. pH modifying agents, as used herein, refer to agents that can be used to adjust the pH of the dentifrice compositions to the above-identified pH range. pH modifying agents may include alkali metal hydroxides, ammonium hydroxide, organic ammonium compounds, carbonates, sesquicarbonates, borates, silicates, phosphates, imidazole, and mixtures thereof. Specific pH agents include monosodium phosphate (monobasic sodium phosphate), trisodium phosphate (sodium phosphate tribasic dodecahydrate or "TSP"), sodium benzoate, benzoic acid, sodium hydroxide, potassium hydroxide, alkali metal carbonate salts, sodium carbonate, imidazole, pyrophosphate salts, sodium gluconate, lactic acid, sodium lactate, citric acid, sodium citrate, phosphoric acid. In one embodiment, 0.01% to 3%, preferably from 0.1% to 1% of TSP by weight of the composition, and 0.001% to 2%, preferably from 0.01% to 0.3% of monosodium phosphate by weight of the composition is used. Without wishing to be bound by theory, TSP and monosodium phosphate may also have calcium ion chelating activity and therefore provide some monofluorophosphate stabilization (in those formulations containing monoflurophospahte).

Anti-Calculus Agent

The dentifrice compositions may include an effective amount of an anti-calculus agent, which in one embodiment may be present from about 0.05% to about 50%, by weight of the composition, alternatively from about 0.05% to about 25%, alternatively from about 0.1% to about 15% by weight of the composition. Non-limiting examples include those described in US 2011/0104081 A1 at paragraph 64, and those described in US 2012/0014883 A1 at paragraphs 63 to 68, as well as the references cited therein. One example is a pyrophosphate salt as a source of pyrophosphate ion. In one embodiment, the composition comprises tetrasodium pyrophosphate (TSPP) or disodium pyrophosphate or combinations thereof, preferably 0.01% to 2%, more preferably from 0.1% to 1% of the pyrophosphate salt by weight of the composition. Without wishing to be bound by theory, TSPP may provide not only calcium chelating thereby mitigating plaque formation, but also may also provide the additional benefit of monofluorophosphate stabilization (in those formulations containing monofluorophosphate).

Surfactant

The dentifrice compositions herein may include a surfactant. The surfactant may be selected from anionic, nonionic, amphoteric, zwitterionic, cationic surfactants, or mixtures thereof. The composition may include a surfactant at a level of from about 0.1% to about 10%, from about 0.025% to about 9%, from about 0.05% to about 5%, from about 0.1% to about 2.5%, from about 0.5% to about 2%, or from about 0.1% to about 1% by weight of the total composition. Non-limiting examples of anionic surfactants may include those described at US 2012/0082630 A1 at paragraphs 32, 33, 34, and 35. Non-limiting examples of zwitterionic or amphoteric surfactants may include those described at US 2012/0082630 A1 at paragraph 36; cationic surfactants may include those described at paragraphs 37 of the reference; and nonionic surfactants may include those described at paragraph 38 of the reference. In one embodiment the composition comprises 0.1% to 5%, preferably 0.1% to 3%, alternatively from 0.3% to 3%, alternatively from 1.2% to 2.4%, alternatively from 1.2% to 1.8%, alternatively from 1.5% to 1.8%, alternatively combinations thereof, of the anionic surfactant sodium lauryl sulfate (SLS) by weight of the composition.

Thickening Agent

The dentifrice compositions herein may include one or more thickening agents. A thickening agent may be used in an amount from about 0.01% to about 15%, or from about 0.1% to about 10%, or from about 0.1% to about 5%, by weight of the composition. Non-limiting examples may include those described in US 2008/0081023 A1 at paragraphs 134 to 137, and the references cited therein.

In embodiment, the composition comprises a linear sulfated polysaccharide as a thickening agent. Carrageenans or carrageenins are one example of a linear sulfated polysaccharide. Generally, carrageenans can vary based upon the degree of sulfation that include: Kappa-carrageenan, Iota-carrageenan, and Lambda-carrageenan. Combinations of carrageenans can be used. In one embodiment, the composition contains from 0.1% to 3% a linear sulfated polysaccharides by weight of the composition, preferably from 0.5% to 2%, alternatively from 0.6% to 1.8%, alternatively combinations thereof. In one embodiment, Iota-carrageenan is used.

In one embodiment, the composition comprises a silica agent, preferably a thickening silica obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167). In one embodiment, the composition comprising from 0.5% to 5% by weight of the composition of a silica agent, preferably from 1% to 4%, alternatively from 1.5% to 3.5%, alternatively from 2% to 3%, alternatively from 2% to 5% alternatively from 1% to 3%, alternatively combinations thereof by weight of the composition.

In one embodiment, the composition comprises a carboxymethyl cellulose ("CMC"). CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9 M3SF Aqualon™ TM9A; Aqualon™ TM12A). In one embodiment, the composition contains from 0.1% to 3% of a CMC by weight of the composition, preferably from 0.5% to 2%, alternatively from 0.6% to 1.8%, alternatively combinations thereof by weight of the composition.

In yet another embodiment, the thickener agents may comprise liner sulfated polysaccharide (e.g., carrageenans), CMC, and preferably also a thickening silica for purposes of cost savings while achieving the right balancing of viscosity and elasticity. In one embodiment, the composition comprises a thickener comprising: (a) 0.01% to less than 1.4%, preferably from 0.1% to 1.3%, more preferably from 0.5% to 1.3% of a carrageenan by weight of the dentifrice composition; and (d) greater than 0.4 wt % to 2 wt %, preferably from 0.5% to 1.8%, more preferably from 0.6% to 1.8% of a carboxymethyl cellulose (CMC) by weight of the dentifrice composition. In yet another embodiment, the aforementioned thickener further comprises 0.5% to 5%, preferably 1% to 4%, of a thickening silica by weight of the dentifrice composition.

Low or Free Humectants

The compositions herein may be substantially free or free of humectants, alternatively contain low levels of humectants. The term "humectant," for the purposes of present invention, include edible polyhydric alcohols such as glycerin, sorbitol, xylitol, butylene glycol, propylene glycol, and combinations thereof. In one embodiment, the humectant is selected from sorbitol, glycerin, and combinations thereof. In yet another embodiment, the humectant is sorbitol. In one embodiment, the composition comprises from 0% to less than 20% of humectants by weight of the composition, preferably from 0% to 10%, alternatively from 0% to 5%, alternatively from 0% to 3%, alternatively from 0% to 2%, alternatively from 0% to 1%, alternatively less than 20%, or less than 19%, 18%, 15%, 12%, 8%, 7%, 6%, 4%, 3%, 2%, 1%, or less than 0.5%; or greater than 1%, or greater than 2%, 5%, 10%, or 15%; or combinations thereof, by weight of the composition. In yet another embodiment, the composition contains less than 20% of sorbitol by weight of the composition.

In an alternative embodiment, the compositions of the present invention comprise a humectant, preferably from 1% to 15% by weight of the composition.

Colorant

The compositions herein may include a colorant. Titanium dioxide is one example of a colorant. Titanium dioxide is a white powder which adds opacity to the compositions. Titanium dioxide generally can comprise from about 0.25% to about 5%, by weight of the composition.

Flavorant

The compositions herein may include from about 0.001% to about 5%, alternatively from about 0.01% to about 4%, alternatively from about 0.1% to about 3%, alternatively from about 0.5% to about 2%, alternatively 1% to 1.5%, alternatively 0.5% to 1%, alternatively combinations thereof, of a flavorant composition by weight of the composition. The term flavorant composition is used in the broadest sense to include flavor ingredients, or sensates, or sensate agents, or combinations thereof. Flavor ingredients may include those described in US 2012/0082630 A1 at paragraph 39; and sensates and sensate ingredients may include those described at paragraphs 40-45, incorporated herein by reference. Excluded from the definition of flavorant composition is "sweetener" (as described above).

Data

Analytical Methods

Experimental and control formulation examples are provided in FIG. 1. These examples are inoculated with a *Halomonas* strain to test each example's ability to inhibit microbial growth at time points of 3 hours, 24 hours, 72 hours, 7 days, and 14 days. The methodology followed is generally according to "Antimicrobial Effectiveness Testing" found in the USP/NF <51> and "Efficacy of Antimicrobial Preservation" found in the European Pharmacopoeia <5.1.3>

As previously discussed, *Halomonas* is chosen because of its ability to successfully grow in a variety of temperature and pH conditions with specific mention to alkaline pH. See e.g., Lee, J C, Jeon, C O, Lim, J M, Lee, S M, Lee, J M, Song, S M, Park, D J, Li, W J, Kim, C J. (2005). *Halomonas taeanensis* sp. nov., a novel moderately halophilic bacterium isolated from a solar saltern in Korea." *Int J Syst Evol Microbiol* 55(Pt 5):2027-32; Romano, I, Giordano, A, Lama, L, Nicolaus, B, Gambacorta, A. (2005) *Halomonas campaniensis* sp. nov., a haloalkaliphilic bacterium isolated from a mineral pool of Campania Region, Italy. *Syst Appl Microbiol* 28(7):610-8; Romano, I., Lama, L., Nicolaus, B., Poli, A., Gambacorta, A. & Giordano, A. (2006). *Halomonas alkaliphila* sp. nov., a novel halotolerant alkaliphilic bacterium isolated from a salt pool in Campania (Italy). *J Gen Appl Microbiol* 52, 339-348; and Wu, G., Wu, X.-Q., Wang, Y.-N., Chi, C.-Q., Tang, Y.-Q., Kida, K., Wu, X.-L. & Luan, Z.-K. (2008). *Halomonas daqingensis* sp. nov., a moderately halophilic bacterium isolated from an oilfield soil. *Int J Syst Evol Microbiol* 58, 2859-2865.

A brief summary of the methodology includes inoculating each example between $1\times10^5$ to $1\times10^6$ cfu/g (colony forming units/gram) of the *Halomonas* strain. At selected time intervals, each test material is stirred at 800 rotations per minute with a overhead stirrer for 5 minutes to make sure it is homogenous and then the stirred sample is assessed for bacteria log reduction. Dilutions and plating are performed to recover and calculate the estimated concentration of the surviving organisms on a logarithm base 10 ($Log_{10}$) scale. $Log_{10}$ reduction estimates at each time interval for each example (provided in Table 1 below) are determined by subtracting the counted concentration from the initial theoretical concentration.

Table 1 below summarizes the examples and the $Log_{10}$ reduction estimates at each time interval. A $Log_{10}$ reduction concentration of 4.2 indicates maximum reduction.

TABLE 1

| Formula | Preservative (wt %) | $Log_{10}$ reduction 3 hrs | $Log_{10}$ reduction 24 hrs | $Log_{10}$ reduction 72 hrs | $Log_{10}$ reduction 7 days |
|---|---|---|---|---|---|
| Ex 1 | BA (0.29) | 1.0 | 2.6 | 4.2 | 4.2 |
| Ex 2 | PA (0.11) | 0.5 | −1.0 | −0.3 | −0.3 |
| Ex 3* | BA (0.2); PA (0.08) | 0.9 | 1.8 | 4.2 | 4.2 |
| Ex 4* | BA (0.2); PA (0.04) | 0.17 | 0.8 | 1.5 | 1.7 |
| Ex 5 | BA (0.1); PA (0.08) | 0.1 | −0.7 | 0.6 | −0.3 |
| Ex 6 | BA (0.1); PA (0.04) | −0.1 | −1.1 | −0.5 | −0.3 |
| Ex 7* | BA (0.29); PA (0.11) | 4.2 | 4.2 | 4.28 | 4.2 |
| Ex 8 Control B | None (Menthol) | −0.3 | 0.5 | −0.3 | −0.3 |
| Ex 9 Control C | PA (0.08) | −1.0 | −1.3 | −0.5 | 1.3 |
| Ex 10 Control D | BA (0.2) | −0.3 | −0.3 | −0.2 | 1.6 |
| Ex 11 Control A | None | −0.1 | 1.2 | −0.6 | 0.7 |

Examples 3, 4, and 7 are dentifrice formulations of the present invention. Example 7, notably having benzyl alcohol (BA) at 0.29 weight percent (wt %) and paraben (PA) at 0.11%, demonstrates maximum reduction in only 3 hours. This is contrast to Example 1 having the same level of BA at 0.29 wt % (but no PA) yet only achieving maximum reduction at 72 hours (i.e., about 24 times longer). Example 2 has the same level of PA at 0.11 wt % (but no BA) yet does not achieve maximum reduction until after 7 days. However, when the combination of BA and PA is used, synergy is demonstrated by Example 7.

Example 3 is an inventive formulation achieving maximum reduction within 72 hours as compared to control formulations. Example 3 has BA at 0.2 wt % and PA is 0.08 wt %. Comparing inventive Example 3 to the controls, Example 10 (Control D) has the same amount of BA (0.2 wt %) but no PA. Maximum reduction is not achieved even after 7 days. Example 9 (Control C) has the same level of PA (0.08 wt %) as inventive Example 3; however, maximum reduction is not achieved at least after 7 days. However, as demonstrated by Example 3, synergy is demonstrated by the combination of BA and PA at the indicated levels by achieving maximum reduction in 72 hours.

Although perhaps not as dramatic, Example 4 also demonstrates synergy between BA and PA by achieving 1.5 $Log_{10}$) reduction in 72 hours. Example 4 has BA at 0.2 wt % and PA at 0.04 wt %. Comparing to inventive Example 4 to the controls, Example 10 (Control D) having the same amount of BA but no PA fails to achieve any $Log_{10}$) reduction at the comparable 72 hours. Similarly Example 9 (Control C) having twice the amount of PA but no BA fails to achieve any $Log_{10}$) reduction at the comparable 72 hours. However, as demonstrated by Example 4, synergy is demonstrated by the combination of BA and PA at the indicated levels by achieving 1.5 $Log_{10}$ reduction in 72 hours while controls cannot.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dentifrice composition comprising:
    (a) 55% to 65% water, by weight of the composition;
    (b) 25% to 40% of a calcium-containing abrasive by weight of the composition;
    (c) greater than 0.15% to 0.30% benzyl alcohol, by weight of the composition;
    (d) 0.03% to 0.11% of a paraben, by weight of the composition; and
    (e) an alkaline pH;
    (f) less than 4% of a humectant selected from the group consisting of glycerin, sorbitol, xylitol, butylene glycol, propylene glycol, and combinations thereof, by weight of the composition;

(g) optionally from 0.1% to 15% polyethylene glycol, by weight of the composition;
wherein the composition is a dentifrice.

2. The composition of claim 1, wherein the alkaline pH is greater than 8.0.

3. The composition of claim 1 wherein the paraben is selected from methyl paraben, propyl paraben, or combinations thereof.

4. The composition of claim 3, wherein the paraben comprises a combination of methyl paraben and propyl paraben, wherein there is a greater weight ratio of methyl paraben to propyl paraben.

5. The composition of claim 1, further comprising 0.0025% to 2% of a fluoride ion source by weight of the composition.

6. The composition of claim 1 further comprising 0.1% to 12% of an anionic surfactant by weight of the composition.

7. The composition of claim 1, further comprising 0.01% to 2% of menthol by weight of the composition.

8. The composition of claim 1, wherein the alkaline pH is from 9 to 12.

9. The composition of claim 1, further comprising:
(a) 0.01% to less than 1.4%, carrageenan, by weight of the composition; and
(b) greater than 0.4% to 2% of a carboxymethyl cellulose, by weight of the composition.

10. The composition of claim 9, further comprising 0.5% to 5% of a thickening silica, by weight of the composition.

11. A method of treating tooth enamel comprising the step of brushing teeth with an oral care composition of claim 1.

12. The composition of claim 1, wherein the abrasive comprises calcium carbonate.

13. The composition of claim 4 wherein the composition comprises from 0.01% to 0.04% propyl paraben and 0.02% to 0.07% methyl paraben.

14. The composition of claim 5 wherein the fluoride ion source is selected from the group consisting of stannous fluoride, sodium fluoride, potassium fluoride, amine fluoride, sodium monofluorophosphate, zinc fluoride, and combinations thereof.

15. A dentifrice composition comprising:
(a) 55% to 65% water, by weight of the composition;
(b) 25% to 40% of a calcium-containing abrasive by weight of the composition;
(c) a preservative comprising 0.15% to 0.30% benzyl alcohol, from 0.01% to 0.04% propyl paraben and 0.02% to 0.07% methyl paraben, by weight of the composition; and
(d) a pH from 8 to 13;
wherein the composition is a dentifrice.

16. The dentifrice composition of claim 15 wherein the ratio of weight ratio of methyl paraben to propyl paraben is from 5:3 to 15:3.

17. The dentifrice composition of claim 15 wherein the composition comprises less than 4% of a humectant selected from the group consisting of glycerin, sorbitol, xylitol, butylene glycol, propylene glycol, and combinations thereof.

18. The dentifrice of claim 1 wherein the composition comprises greater than 0.18% to 0.30% benzyl alcohol, by weight of the composition.

19. The dentifrice of claim 15 wherein the composition comprises greater than 0.18% to 0.30% benzyl alcohol, by weight of the composition.

20. The dentifrice of claim 19 wherein the composition comprises 0.01% to 0.03% propyl paraben and 0.03% to 0.05% methyl paraben.

* * * * *